United States Patent [19]

Wong

[11] Patent Number: 5,540,331
[45] Date of Patent: Jul. 30, 1996

[54] LEAK PROOF VIAL FOR MICROSCOPE SLIDES

[75] Inventor: Johnson N. S. Wong, Rolling Hills, Calif.

[73] Assignee: Evergreen Industries, Inc., Los Angeles, Calif.

[21] Appl. No.: 366,869

[22] Filed: Dec. 30, 1994

[51] Int. Cl.$^6$ .................................................. B65D 85/48
[52] U.S. Cl. ................. 206/456; 215/6; 220/555
[58] Field of Search ............................. 206/456; 215/6, 215/343, 341; 220/553, 554, 555

[56] References Cited

U.S. PATENT DOCUMENTS

| | | | |
|---|---|---|---|
| 748,329 | 12/1903 | Williamson | 215/6 |
| 3,063,549 | 11/1962 | Weichselbaum | 206/456 |
| 3,651,926 | 3/1972 | Elfast, Jr. | 206/456 |
| 4,078,937 | 3/1978 | Tani et al. | |
| 4,209,102 | 6/1980 | Dunn et al. | 215/344 |
| 4,635,790 | 1/1987 | Jackson et al. | 206/456 |
| 4,635,791 | 1/1987 | Jackson et al. | 206/456 |
| 4,724,855 | 2/1988 | Jackson et al. | 215/6 |
| 4,770,309 | 9/1988 | Thompson | 215/344 |
| 4,772,558 | 9/1988 | Hammann | 215/6 |

OTHER PUBLICATIONS

Evergreen Scientific Catalog showing, Slide Mailers, published prior to Dec. 30, 1993.
Evergreen Scientific Catalog showing, Formalin Vials, published prior to Dec. 30, 1993.

*Primary Examiner*—David T. Fidei
*Attorney, Agent, or Firm*—Robbins, Berliner & Carson

[57] ABSTRACT

A solvent-leak-proof container for rectangular microscope slides includes a thermoplastic vial formed with a threaded cylindrical end and a removable threaded mating cap. The cap includes a centrally disposed cylindrical sealing member for leak proof sealing against the threaded end of the vial. The vial interior includes opposing pairs of longitudinal ribs for supporting and positioning rectangular microscope slides within the vial. The body of the vial is circular at least at the threaded end mating with the cap, but is generally rectangular thereafter to form opposing pairs of flat gripping surfaces which are also suitable for marking the vial for identification.

9 Claims, 1 Drawing Sheet

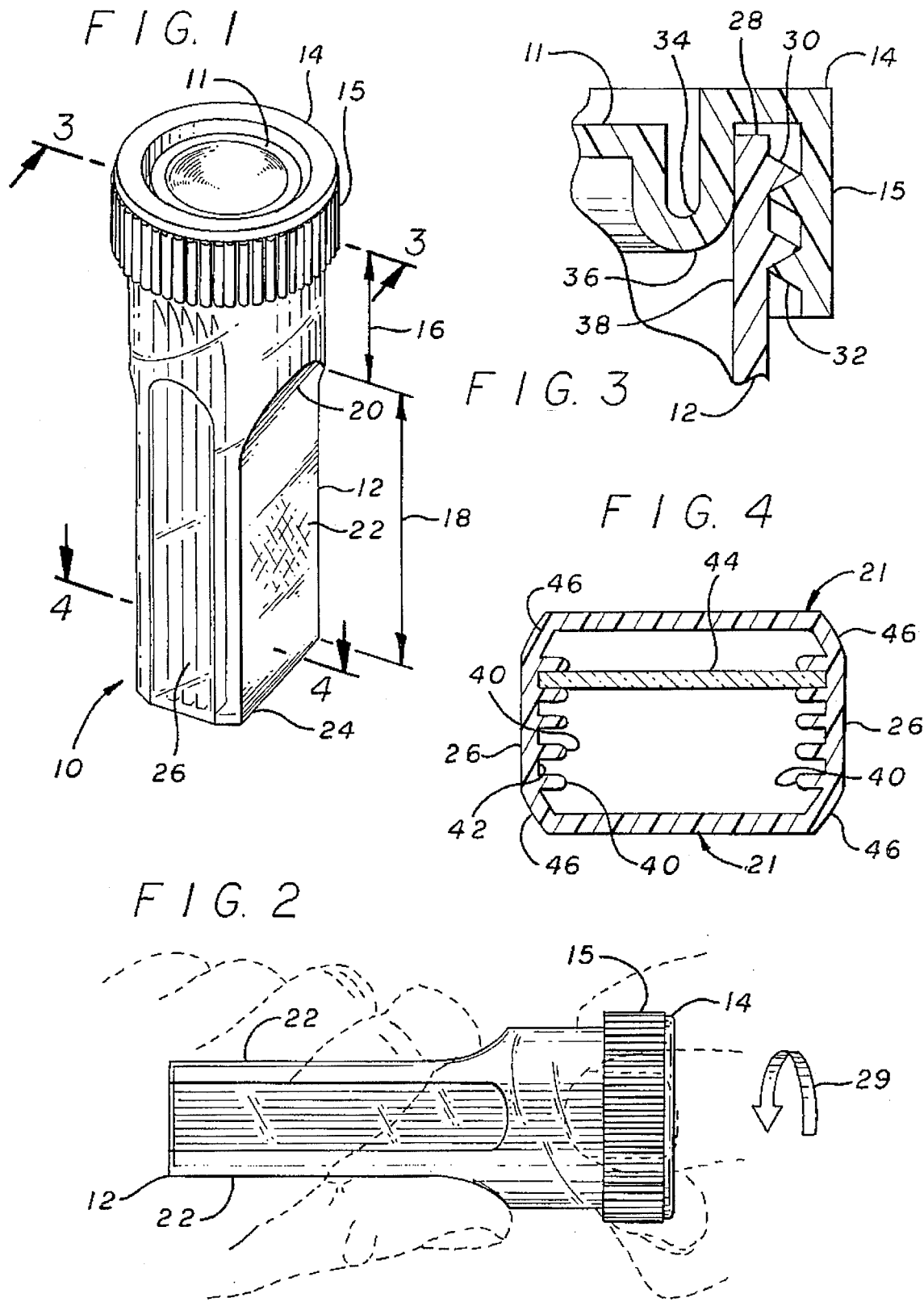

5,540,331

LEAK PROOF VIAL FOR MICROSCOPE SLIDES

BACKGROUND OF THE INVENTION

1. Field of the Invention

This invention relates to leak proof containers for holding and processing medical slides, such as staining jars, slide storage and mailing jars, pap jars, formalin vials and the like.

2. Description of the Prior Art

Many different conventional slide containers have desirable qualities related to their materials of construction, mechanisms for sealing the slides and liquids in the container, and particular configurations for ease of handling and use. Each of these designs also have substantial limitations in the same areas depending upon the design compromises made during their creation.

What is needed is a sealable jar for containing medical slides in a leak proof manner which is easy and convenient for use and which is not limited by the problems associated with conventional designs.

SUMMARY OF THE INVENTION

The present invention provides, in general, a solvent-leak-proof container for rectangular microscope slides in which a thermoplastic vial is formed with a threaded cylindrical lip end and a removable mating cap is provided with a centrally disposed cylindrical sealing member for leak proof sealing against the lip end of the vial. The vial interior includes opposing pairs of longitudinal ribs for supporting and positioning the rectangular slides within the vial. The body of the vial is circular at least at the lip end mating with the cap, but may be generally rectangular at the opposite end thereof for ease of use during gripping and marking the vial for identification.

In one aspect, the present invention provides a solvent-leak-proof jar for containing at least one rectangular microscope slide. The jar includes a vial and a mating cap. The vial has a cylindrical, screw threaded top lip and at least two opposing pairs of longitudinal ribs. The ribs of each pair are spread from each other a distance that is at least the thickness of each slide. The pairs of ribs are disposed in repetitive opposite inside surfaces of the vial for holding the slides. The mating cap for the vial has an internal screw thread mating with the screw thread of the vial top lip. The cap includes a centrally disposed cylindrical sealing member against which the vial lip is seated when the cap is threaded onto the vial.

These and other features and advantages of this invention will become further apparent from the detailed description and accompanying figures that follow. In the figures and description, numerals indicate the various features of the invention, like numerals referring to like features throughout both the drawings and the description.

BRIEF DESCRIPTION OF THE DRAWINGS

FIG. 1 is an isometric view of a vial sealed with a cap in accordance with the present invention.

FIG. 2 is a side view of the vial and cap of FIG. 1 illustrating the manner in which the vial body may be held with one hand while the cap may be tightened or loosened with the other hand.

FIG. 3 is a partial cross section view of the circular portion of the vial and cap combination of FIG. 1 taken along line 3—3.

FIG. 4 is a cross section view of the rectangular portion of the vial of FIG. 1, taken along line 4—4, showing the internal ribs holding a slide in position with the vial.

DETAILED DESCRIPTION OF THE PREFERRED EMBODIMENT(S)

FIG. 1 is an isometric view of leak proof slide container or jar 10, according to the present invention, in which vial 12 is sealed by circular cap 14. The upper end of vial 12 mates with circular cap 14 and is, of course, also circular in cross section. Cap 14 is preferably provided with a gripping surface, such as gripping ribs 15, which is relatively easy to grasp firmly by hand. The center of cap 14 includes integral seal 11 shown and described in greater detail with respect to FIG. 3. Although the circular cross section of the body of vial 12 may extend the length of vial 12, in the preferred embodiment shown in FIG. 1 the circular cross section of vial 12 extends away from cap 14 for a convenient distance such as distance 16.

Vial 12 has a length substantially greater than its width and the remainder of the body of vial 12 is preferably not cylindrical. In particular, the remainder of the body of vial 12 is generally rectangular in cross-section, for a convenient distance such as distance 18, as will be described in greater detain below particularly with respect to FIG. 2. A portion of at least two opposing faces, gripping faces 21, of the rectangular cross sectional portion of vial 12 along distance 18 is a transition portion, one of which is shown in FIG. 1 as gripping ridge 20. The remainder of each of said two opposing faces is a flat gripping surface such as flat gripping surface 22 which extends from gripping ridge 20 to the bottom end 24 of vial 12. Bottom end 24 of vial 12 is preferably sealed and flat so that leak proof slide container 10 may conveniently be stood upright with closed bottom end 24 on a flat surface, such as a table or counter top, while cap 14 is then conveniently available at the upper end of vial 12.

As shown and described below in greater detail with respect to FIG. 2, the pair of gripping ridges 20, and the pair of flat gripping surfaces 22, are used during sealing and unsealing of cap 14 to vial 12. The remaining two opposing faces, rib faces 26, of the portion of vial 12 along distance 18 are generally orthogonal to flat gripping surfaces 22 and are also preferably flat surfaces for handling convenience although they may also be partially or fully rounded for particular applications.

Referring now to FIG. 2, vial 12 is shown in a side view in a generally horizontal position grasped by a human left hand shown in partial dotted outline. Cap 14 is shown fastened to vial 12 and is grasped by a human right hand shown in partial dotted outline so that it can be unscrewed by counterclockwise rotation as indicated by arrow 29. Obviously, cap 14 is fastened to vial 12 by rotation in the opposite direction.

During fastening and removal of cap 14 from vial 12, gripping ribs 15 provide a secure gripping surface for the hand manipulating cap 14. Similar, the pair of opposing flat gripping surfaces 22 serve to provide a secure pair of opposed gripping surfaces to be grasped between the thumb and fingers of the hand manipulating vial 12. In addition, as noted above with respect to FIG. 1, each flat gripping surface 22 includes a gripping ridge 20 as a transition between the rectangular cross section of vial 12 at closed bottom end 24 and the circular cross section at the end of vial 12 near cap 14.

Referring now to FIG. 3, a partial cross sectional view of the circular portion of vial 12 and cap 14 of leak proof slide container 10 is shown taken along line 3—3 of FIG. 1. In particular, a portion of circular lip 28, the end of vial 12 opposite closed bottom end 24, is shown in which male threads 30 are mated with female threads 32 of cap 14. By tightening cap 14 on circular lip 28 of vial 12, the contents of leak proof slide container 10 may be sealed to prevent leakage or contamination of the contents thereof.

In accordance with the preferred embodiment shown, cap 14 includes integral seal 11 to provide a more secure seal. Although some sealing between circular lip 28 of vial 12 and cap 14 may occur if the cap is tightened sufficiently so that circular lip 28 actually contacts the flat lower surface of cap 14, a substantially improved sealing arrangement is created between integral seal 11 and the inner surface circular lip 28.

In particular, integral seal 11 is positioned within the center of cap 14 so that a downward facing U shaped depression in the material of cap 14 forms integral cap O-ring seal 34 within cap 14. Although an integral O-ring is shown in the preferred embodiment, the generally circular cross-sectional shape of integral cap O-ring seal 34 may be formed, and or added to cap 14, in other ways. In operation, as circular lip 28 is threaded into cap 14, at least some portion of circular lip 28 comes into contact with integral cap O-ring seal 34 to form a substantially better leak proof seal that would be accomplished solely by contact between the upper surface of circular lip 28 and the bottom surface of cap 14.

In accordance with the preferred embodiment shown in FIG. 3, the lower, rounded peripheral surface of integral cap O-ring seal 34, cap sealing ring surface 36, is contacted by the upper end and inner cylindrical surface 38 of circular lip 28. When fully closed, cap sealing ring surface 36 forms a leak proof seal against inner cylindrical surface 38 completing leak proof slide container 10.

Referring now to FIG. 4, a cross section view of rectangular portion of vial 12, taken along line 4—4 of FIG. 1, is shown detailing the internal ribs holding the microscope slides within leak proof slide container 10 in position. For the purposes of illustration, the vial shown in this figure can accommodate a maximum of four slides, but configurations with other numbers of slides are well within the spirit and scope of this invention. Each rib face 26 of vial 12 has five ribs 40 providing a series of four slots 42 formed therebetween. Ribs 40 and slots 42 on each rib faces 26 are positioned laterally adjacent from each other so that microscope slides or similar devices may be positioned within each pair of opposing slots 42 formed between pairs of opposing ribs 40. In particular, microscope slide 44 is shown for illustration positioned within the upper most pair of opposing slots 42 shown in FIG. 4.

In addition to opposed gripping faces 22, and opposed rib faces 26, vial 12 may conveniently includes generally rounded transition edges 46. The lack of relatively sharp edges between the gripping and rib faces provides for a more comfortable grasp by a human hand during sealing and unsealing of leak proof slide container 10. The cross sectional area remains generally rectangular so that, if necessary, vial 12 may be grasped by a tool such as a wrench or other slot like structure to aid in unsealing a tightly sealed or jammed cap 14. The generally rectangular cross sectional of vial 12 near closed bottom end 24 also provides for convenient mounting for storage and use.

In general, leak proof slide container 10 is preferably made from a suitable thermoplastic material impervious to the liquids such as alcohol, formaldehyde and the like which are commonly associated with the storage and transport of microscope slides in a vial. In addition, it is convenient to roughen the surface of at least one or both flat gripping surfaces 22, as indicated in FIG. 1. The roughened surface further aids gripping and also provides a convenient location for marking by pencil, felt tip pen or other convenient means.

Having now described the invention in accordance with the requirements of the patent statutes, those skilled in this art will understand how to make changes and modifications in the present invention to meet their specific requirements or conditions. Such changes and modifications may be made without departing from the scope and spirit of the invention as set forth in the following claims.

What is claimed is:

1. A solvent-leak-proof jar for containing at least one rectangular microscope slide, comprising:

a vial having a cylindrical, screw threaded top lip and a non-cylindrical section having a length substantially greater than its width extending from the cylindrical threaded top lip, said non-cylindrical section forming a pair of opposed flat gripping surfaces;

a cap for said vial having an integral screw thread mating with the screw thread of said vial top lip and having a centrally disposed cylindrical sealing member against which said vial lip is seated when said cap is threaded onto said vial; and at least two opposing pairs of longitudinal ribs in the vial, the ribs of each pair being spread from each other a distance that is at least the thickness of each slide, said pairs of ribs being disposed in repetitive opposite inside surfaces of said vial for holding said slides therein.

2. The invention of claim 1, wherein each of said flat gripping surfaces further comprises:

a gripping ridge forming a transition from the flat gripping surface to the cylindrical lip.

3. The invention of claim 1, wherein each of said flat gripping surfaces further comprises:

a surface suitable for marking.

4. The invention of claim 3, wherein said surface suitable for marking is a roughened thermoplastic.

5. The invention of claim 1, wherein the non-cylindrical cross section of the vial is generally rectangular in cross section.

6. The invention of claim 1, wherein the non-cylindrical cross section of the vial further comprises;

a pair of opposed rib surfaces supporting said ribs, said rib surfaces being generally orthogonal to the gripping surfaces.

7. The invention of claim 1, wherein said vial is formed of a thermoplastic material.

8. The invention of claim 1, wherein said centrally disposed cylindrical member further comprises:

an integral U shaped depression formed in said cap.

9. The invention of claim 1, wherein said cap further comprises:

peripheral external gripping ribs extending along the direction of the length of the vial.

\* \* \* \* \*